United States Patent [19]

Seidel et al.

[11] Patent Number: 5,674,676
[45] Date of Patent: Oct. 7, 1997

[54] HCV PEPTIDE ANTIGENS AND METHOD OF DETERMINING HCV

[75] Inventors: Christoph Seidel, Weilheim; Ursula-Henrike Wienhues, München; Hubert Bayer, Weilheim; Guenther-Gerhard Jung; Hans Georg Ihlenfeldt, both of Tübingen, all of Germany

[73] Assignee: Boehringer Mannheim GmbH, Mannheim, Germany

[21] Appl. No.: 102,738

[22] Filed: Aug. 6, 1993

[30] Foreign Application Priority Data

Aug. 7, 1992 [DE] Germany .......................... 42 26 093.0
Dec. 5, 1992 [DE] Germany .......................... 42 40 980.2

[51] Int. Cl.⁶ .......................... C12Q 1/70; A61K 39/29; A61K 14/18; C07K 5/107
[52] U.S. Cl. .......................... 435/5; 424/189.1; 530/326; 530/327; 530/328; 530/329; 530/330
[58] Field of Search .......................... 530/326, 327, 530/328, 329, 330; 424/189.1; 435/5

[56] References Cited

U.S. PATENT DOCUMENTS

| | | | |
|---|---|---|---|
| 5,106,726 | 4/1992 | Wang | 435/5 |
| 5,350,671 | 9/1994 | Houghton et al. | 435/5 |

FOREIGN PATENT DOCUMENTS

| | | |
|---|---|---|
| 0269092 | 6/1988 | European Pat. Off. |
| 0318216 | 5/1989 | European Pat. Off. |
| 0363025 | 4/1990 | European Pat. Off. |
| 0442394 | 8/1991 | European Pat. Off. |
| 0445801 | 9/1991 | European Pat. Off. |
| 0464287 | 1/1992 | European Pat. Off. |
| 0468527 | 1/1992 | European Pat. Off. |
| 0484787 | 5/1992 | European Pat. Off. |
| 0489968 | 6/1992 | European Pat. Off. |
| WO9212992 | 8/1992 | WIPO. |
| WO9217493 | 10/1992 | WIPO. |
| 9300365 | 1/1993 | WIPO .......................... C07K 15/04 |

OTHER PUBLICATIONS

Okamote et al., Japan, "Enzyme–Linked Immunoabsorbent Assay for Antibodies Against the Capsid Protein of Hepatitis C Virus with a Synthetic Oligopeptide", J. Exp. Med. vol. 60.4, pp. 223–233.

Munekata et al., in Shimonishi (Ed), Peptide Chemistry, 1990; "Epitope–Mapping of Hepatitis C Virus Constituting Protein", pp. 223–233.

Van Der Poel et al., "Confirmation of Hepatitis C Virus Injection by new four–antigen recombinant immunoblot assay", Lancet vol. 337, p. 337, Feb. 9, 1991.

Kuo et al., "An assay for circulating Antibodies to a Major Etiologic Virus of Human Non–A, Non–B Hepatitis", Science vol. 224, No. 4901, 362–364, Apr. 1989.

Merrifield, "Solid Phase Peptide Synthesis, I. The Synthesis of a Tetrapeptide", JACS, 2149, 2149–2154, Jul. 10, 1963.

Leary et al., "Rapid and Sensitive Colorimetric Method for Visualizing Biotin–labelled DNA Probes Hybridized to DNA or RNA Immobilized on Nitrocellulose: Bio–blots", PNAS vol. 8, 4045–4049, Jul. 1983.

Wang, JACS, 95:4, pp. 1328–1333 (1973).

Alter, Journal of Gastroenterology and Hepatology (1990), Suppl. 1, 78–94.

Choo et al, "Insolation of cDNA Clone Derived from a Blood Borne Non–A, Non–B Viral Hepatitis Genome", Science 244, 359–361, Apr. 21, 1989.

Farci et al., "Lack of Protective Immunity Against Reinfection with Hepatitis C Virus," Science 258:135–140 (1992).

*Primary Examiner*—Michael P. Woodward
*Attorney, Agent, or Firm*—Felfe & Lynch

[57] ABSTRACT

New HCV peptide antigens are described. These peptide antigens are suitable for the determination of HCV antibodies as immunogens for the preparation of antibodies to HCV and as immunogens for the preparation of vaccines to HCV.

5 Claims, No Drawings

SEQUENCE LISTING ( 1 ) GENERAL INFORMATION:

( i i i ) NUMBER OF SEQUENCES: 28

( 2 ) INFORMATION FOR SEQ ID NO: 1:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 1:

```
Leu Asp Gly Val Arg Leu His Arg Phe Ala Pro Pro Cys Lys Pro Leu
 1               5                  10                      15
Leu Arg
```

( 2 ) INFORMATION FOR SEQ ID NO: 2:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 2:

```
Leu His Gln Trp Ile Ser Ser Glu Cys Thr Thr Pro Cys Ser Gly Ser
 1               5                  10                      15
Trp Leu Arg Asp Ile
                20
```

( 2 ) INFORMATION FOR SEQ ID NO: 3:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 3:

```
Ser Arg Arg Phe Ala Gln Ala Leu Pro Val Trp Ala Arg Pro Asp
```

( 2 ) INFORMATION FOR SEQ ID NO: 4:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 4:

```
Asn Lys Val Val Ile Leu Gly Ser Phe Asp Pro Leu Val Ala Glu Glu
 1               5                  10                  15
Asp Glu Arg Glu Ile
                20
```

( 2 ) INFORMATION FOR SEQ ID NO: 5:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 5:

```
Pro Ser His Ile Thr Ala Glu Ala Ala Gly Arg Arg Leu Ala Arg Gly
 1               5                  10                  15
```

( 2 ) INFORMATION FOR SEQ ID NO: 6:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 6:

```
Ser Arg Gly Asn His Val Ser Pro Thr His Tyr Val Pro Glu Ser Asp
 1               5                  10                  15
Ala Ala
```

( 2 ) INFORMATION FOR SEQ ID NO: 7:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 7:

```
His Val Ser Pro Thr His Tyr Val Pro
 1               5
```

( 2 ) INFORMATION FOR SEQ ID NO: 8:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear (i i) MOLECULE TYPE: cDNA (x i) SEQUENCE DESCRIPTION: SEQ ID NO: 8:

Val Ser Pro Thr His Tyr Val Pro Glu
1               5

(2) INFORMATION FOR SEQ ID NO: 9:

(i) SEQUENCE CHARACTERISTICS:
    (A) LENGTH: 10 amino acids
    (B) TYPE: amino acid
    (C) STRANDEDNESS: single
    (D) TOPOLOGY: linear (i i) MOLECULE TYPE: cDNA (x i) SEQUENCE DESCRIPTION: SEQ ID NO: 9:

His Val Ser Pro Thr His Tyr Val Pro Glu
1               5                     10

(2) INFORMATION FOR SEQ ID NO: 10:

(i) SEQUENCE CHARACTERISTICS:
    (A) LENGTH: 9 amino acids
    (B) TYPE: amino acid
    (C) STRANDEDNESS: single
    (D) TOPOLOGY: linear (i i) MOLECULE TYPE: cDNA (x i) SEQUENCE DESCRIPTION: SEQ ID NO: 10:

Ala Leu Pro Val Trp Ala Arg Pro Asp
1               5

(2) INFORMATION FOR SEQ ID NO: 11:

(i) SEQUENCE CHARACTERISTICS:
    (A) LENGTH: 9 amino acids
    (B) TYPE: amino acid
    (C) STRANDEDNESS: single
    (D) TOPOLOGY: linear (i i) MOLECULE TYPE: cDNA (x i) SEQUENCE DESCRIPTION: SEQ ID NO: 11:

Phe Ala Gln Ala Leu Pro Val Trp Ala
1               5

(2) INFORMATION FOR SEQ ID NO: 12:

(i) SEQUENCE CHARACTERISTICS:
    (A) LENGTH: 9 amino acids
    (B) TYPE: amino acid
    (C) STRANDEDNESS: single
    (D) TOPOLOGY: linear (i i) MOLECULE TYPE: cDNA (x i) SEQUENCE DESCRIPTION: SEQ ID NO: 12:

Lys Asn Lys Arg Asn Thr Asn Arg Arg
1               5

(2) INFORMATION FOR SEQ ID NO: 13:

(i) SEQUENCE CHARACTERISTICS:
    (A) LENGTH: 9 amino acids
    (B) TYPE: amino acid
    (C) STRANDEDNESS: single
    (D) TOPOLOGY: linear ( i i ) MOLECULE TYPE: cDNA ( x i ) SEQUENCE DESCRIPTION: SEQ ID NO: 13:

Lys Phe Pro Gly Gly Gly Gln Ile Phe
1               5

( 2 ) INFORMATION FOR SEQ ID NO: 14:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 14:

Gln Asp Val Lys Phe Pro Gly Gly Gly
1               5

( 2 ) INFORMATION FOR SEQ ID NO: 15:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 15:

Ser Gln His Leu Pro Tyr Ile Glu Gln
1               5

( 2 ) INFORMATION FOR SEQ ID NO: 16:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 16:

Gln Lys Ala Leu Gly Leu Leu Gln Thr
1               5

( 2 ) INFORMATION FOR SEQ ID NO: 17:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 17:

Gln Asp Val Lys Phe Pro Gly Gly Gly Gln Ile Val
1               5                   10

( 2 ) INFORMATION FOR SEQ ID NO: 18:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear (i i) MOLECULE TYPE: cDNA (x i) SEQUENCE DESCRIPTION: SEQ ID NO: 18:

Lys Ala Arg Arg Pro Glu Gly Arg Thr Trp Ala Gln Pro Gly Tyr
1               5                   10                  15

(2) INFORMATION FOR SEQ ID NO: 19:

(i) SEQUENCE CHARACTERISTICS:
        (A) LENGTH: 16 amino acids
        (B) TYPE: amino acid
        (C) STRANDEDNESS: single
        (D) TOPOLOGY: linear (i i) MOLECULE TYPE: cDNA (x i) SEQUENCE DESCRIPTION: SEQ ID NO: 19:

Pro Gln Asp Val Lys Phe Pro Gly Gly Gly Gln Ile Val Gly Gly Val
1               5                   10                  15

(2) INFORMATION FOR SEQ ID NO: 20:

(i) SEQUENCE CHARACTERISTICS:
        (A) LENGTH: 15 amino acids
        (B) TYPE: amino acid
        (C) STRANDEDNESS: single
        (D) TOPOLOGY: linear (i i) MOLECULE TYPE: cDNA (x i) SEQUENCE DESCRIPTION: SEQ ID NO: 20:

Leu Leu Leu Leu Ala Ala Gly Val Gly Ile Tyr Leu Leu Pro Asn
1               5                   10                  15

(2) INFORMATION FOR SEQ ID NO: 21:

(i) SEQUENCE CHARACTERISTICS:
        (A) LENGTH: 11 amino acids
        (B) TYPE: amino acid
        (C) STRANDEDNESS: single
        (D) TOPOLOGY: linear (i i) MOLECULE TYPE: cDNA (x i) SEQUENCE DESCRIPTION: SEQ ID NO: 21:

Pro Gly Gly Gln Ile Val Gly Gly Val Tyr Leu
1               5                   10

(2) INFORMATION FOR SEQ ID NO: 22:

(i) SEQUENCE CHARACTERISTICS:
        (A) LENGTH: 12 amino acids
        (B) TYPE: amino acid
        (C) STRANDEDNESS: single
        (D) TOPOLOGY: linear (i i) MOLECULE TYPE: cDNA (x i) SEQUENCE DESCRIPTION: SEQ ID NO: 22:

Gly Gln Ile Val Gly Gly Val Tyr Leu Leu Pro Arg
1               5                   10

(2) INFORMATION FOR SEQ ID NO: 23:

(i) SEQUENCE CHARACTERISTICS:
        (A) LENGTH: 12 amino acids
        (B) TYPE: amino acid
        (C) STRANDEDNESS: single
        (D) TOPOLOGY: linear (i i) MOLECULE TYPE: cDNA (x i) SEQUENCE DESCRIPTION: SEQ ID NO: 23:

Val Gly Gly Val Tyr Leu Leu Pro Arg Arg Gly Pro
1               5                   10

(2) INFORMATION FOR SEQ ID NO: 24:

(i) SEQUENCE CHARACTERISTICS:
        (A) LENGTH: 12 amino acids
        (B) TYPE: amino acid
        (C) STRANDEDNESS: single
        (D) TOPOLOGY: linear (i i) MOLECULE TYPE: cDNA (x i) SEQUENCE DESCRIPTION: SEQ ID NO: 24:

Val Tyr Leu Leu Pro Arg Arg Gly Pro Arg Leu Gly
1               5                   10

(2) INFORMATION FOR SEQ ID NO: 25:

(i) SEQUENCE CHARACTERISTICS:
        (A) LENGTH: 8 amino acids
        (B) TYPE: amino acid
        (C) STRANDEDNESS: single
        (D) TOPOLOGY: linear (i i) MOLECULE TYPE: cDNA (x i) SEQUENCE DESCRIPTION: SEQ ID NO: 25:

Gly Val Tyr Leu Leu Pro Arg Arg
1               5

(2) INFORMATION FOR SEQ ID NO: 26:

(i) SEQUENCE CHARACTERISTICS:
        (A) LENGTH: 6 amino acids
        (B) TYPE: amino acid
        (C) STRANDEDNESS: single
        (D) TOPOLOGY: linear (i i) MOLECULE TYPE: cDNA (x i) SEQUENCE DESCRIPTION: SEQ ID NO: 26:

Val Tyr Leu Leu Pro Arg
1               5

(2) INFORMATION FOR SEQ ID NO: 27:

(i) SEQUENCE CHARACTERISTICS:
        (A) LENGTH: 4 amino acids
        (B) TYPE: amino acid
        (C) STRANDEDNESS: single
        (D) TOPOLOGY: linear (i i) MOLECULE TYPE: cDNA (x i) SEQUENCE DESCRIPTION: SEQ ID NO: 27:

Tyr Leu Leu Pro
1

(2) INFORMATION FOR SEQ ID NO: 28:

(i) SEQUENCE CHARACTERISTICS:
        (A) LENGTH: 17 amino acids
        (B) TYPE: amino acid
        (C) STRANDEDNESS: single
        (D) TOPOLOGY: linear -continued ( i i ) MOLECULE TYPE: cDNA ( x i ) SEQUENCE DESCRIPTION: SEQ ID NO: 28:

| Gly | Gln | Ile | Val | Gly | Gly | Val | Tyr | Leu | Leu | Pro | Arg | Gly | Pro | Arg | Leu |
|---|---|---|---|---|---|---|---|---|---|---|---|---|---|---|---|
| 1 | | | | 5 | | | | | 10 | | | | | 15 | |

Gly

HCV PEPTIDE ANTIGENS AND METHOD OF DETERMINING HCV

The invention addresses new HCV peptide antigens, a process for the production of these peptide antigens, and a method of determining HCV with the aid of these peptide antigens.

The presence of a viral hepatitis in the absence of serological markers of so far unknown hepatotropic agents (e.g. hepatitis A virus, hepatitis B virus, hepatitis C virus, cytomegaly virus and Epstein-Barr virus) is referred to as Non-A-, Non-B-hepatitis (NANB-hepatitis). NANB-hepatitis in turn is subdivided into parenterally and sporadically transmitted Non-A-, Non-B-hepatitis and enterically transmitted Non-A-, Non-B-hepatitis. Recently, the causative agent for parenterally and sporadically transmitted NANB-hepatitis, the hepatitis C virus (HCV), has been isolated (Choo Q.-L. et at., Science 244 (1989) 359–362 and Kuo, G. et al., Science 244 (1989) 362–364).

HCV is an important cause of NANB hepatitis worldwide. The virus is transmitted through contaminated blood or blood products, blood transfers, or by close intimate contact.

The amino acid sequence of the HCV virus proteins is known from EP-A 0 318 216, EP-A 0 363 025, EPA 388 232, and EP-A 0 396 748. The HCV genome has a length of 10862 nucleotides. The proteins synthesized in the translation procedure have a total length of approximately 3000 amino acids. These proteins can be divided into structural proteins (envelope and core proteins) and non-structural proteins (NS1–NS5).

HCV is advantageously determined by detecting antibodies to HCV in body fluids using immunological tests. Such immunological tests therefore require binding partners for anti-HCV antibodies.

It is therefore known, to use the non-structural C 100-3-HCV protein, for example, as a binding partner in an immunological test (tests by Abbott Laboratories, USA, and Ortho Diagnostic Systems Inc., USA; Science 244 (1989) 359–364; Van der Poel C. L. et al., Lancet 337 (1991) 317; Alter H. J., J. Gastroent. Hepatol. (suppl.) 1990, 78).

A drawback of these tests is that the antigen used is a recombinant protein. Proteins are difficult to handle because of their susceptibility to denaturing and their reduced solubility and function in diagnostic tests. As a result of the low epitope density on a protein, even the size of a measuring signal is smaller as compared to tests where a short-chain peptide antigen is used as a binding partner to the antibody. Moreover, when proteins or long-chain peptides are used as antigens in an immunological test, there is an increased chance of cross-reactivities and non-specific binding of antibodies. Reactions with proteins are also frequently diffusion-controlled which is adverse to the desired short assay times for immunological tests. Further, the preparation of sufficient quantities and qualifies of protein to be used in such diagnostic procedures is time- and cost-intensive. As they can be synthesized, peptides are easily accessible and are defined molecules.

In immunological tests for anti-HCV antibodies, it is, hence, advantageous to use peptide antigens with shortest possible chains which represent only segments of the whole protein. Such an immunological method has been described by Okamoto (Japan J. Exp. Met. 60 (1990) 223–234). However it turned out, that a short-chained peptide antigen described therein (sequence 9), whose origin is in the core region, is not sufficiently sensitive for HCV.

Additional HCV peptide antigens are described in German patent application P 42 09 215.9.

The object of the present invention is to provide peptide antigens that are specific for anti-HCV antibodies and suitable for immunological tests for anti-HCV antibodies.

This object is accomplished by the peptide antigens of the following sequences.

7B6: LDGVRLHRFAPPCKPLLR
7A5: LHQWISSECTTPCSGSWLRDI
NS5/1: SRRFAQALPVWARPD
7B12: NKVVILGSFDPLVAEEDEREI
6F10: PSHITAEAAGRRLARG
7A1: SRGNHVSPTHYVPESDAA
8C3: LLLLAAGVGIYLLPN
X: GQIVGGVYLLPRRGPRLG or by peptide antigens which are partial sequences of these peptide antigens covering at least four, preferably at least seven, amino acids in length.

The search for the epitope in sequence X posed certain problems. Corresponding peptides in solution had to brought in contact with antibodies to HCV to subsequently detect the so-formed immunocomplexes. This was achieved by biotinylation of the peptides and immobilization of the complexes on a streptavidin-coated solid phase. The peptides detected are also particularly suited for immunoassays where in-solution complexation is employed. The epitope is located at the C-terminal end directly behind the peptide described under SEQ ID NO 16 in WO 93/01210. At the N-terminal end, it is located in the core region.

Suitable partial sequences are given in the sequence protocols.

The following are particularly preferred partial sequences:

From sequence 7A1:
NS4/3a: HVSPTHYVP
NS4/3b: VSPTHYVPE
NS4/3: HVSPTHYVPE
From sequence NS5/1:
7D/2: ALPVWARPD
NS5/1b: FAQALPVWA
From sequence X:
D2: VYLLPR
D1: GVYLLPRR Particularly preferred partial sequences are those with a maximum length of 9 amino acids, especially the substances NS4/3 and NS5/1b. A particularly preferred peptide antigen is NS5/1.

From sequence X, SEQ ID NO 26 recognizes all examined sera whereas SEQ ID No. 25 is the reactive antigen (greatest signal).

The anti-HCV antibody detection is performed according to methods known to the expert. Another subject matter of the invention is, therefore, a method of determining HCV antibodies which is characterized in that the sample is incubated with at least one peptide antigen from the group of the sequences SEQ ID NO 1–11, 20, and 22–28 or peptide antigens which are partial sequences of these peptide antigens of at least four, preferably at least seven amino acids in length, and in that the amount of anti-HCV antibodies bound to the peptide antigens is determined under conditions which allow the formation of an antibody antigen complex.

The peptide antigens of the invention are preferably used in a concentration range of 1–1000 ng/ml, particularly preferred in a range of 20–250 ng/ml.

In accordance with the invention, a combination of at least two peptide antigens of the invention or partial sequences thereof is preferably used. It is particularly preferred to combine at least one peptide antigen of the sequences SEQ ID NO 1–11, 20 and 22–28 or partial sequences thereof with at least one peptide antigen from the group of the sequences SEQ ID NO 12–19 or partial sequences thereof.

The sequences of SEQ ID NO 12–19 and their preparation are described in German Patent Application P 42 09 215.9, the contents of which is subject matter of the disclosure of the present patent application.

The antigens can, for example, be combined in that several individual peptide antigens are used or in that peptide antigens are bound to one another either covalently, advantageously via an amino acid bridge, which is different from amino acid sequences naturally occurring in HCV proteins or via a peptide linker.

Particularly preferred antigen combinations include:
Sequence 4a, 6e, 6b, 2e, 2g, NS4/3, NS5/1 (combination 1)
Sequence 4a, 6e, 6b, 2e, 2g, NS4/3 (combination 2)
Sequence 4a, 2g, 2e, 6c, NS4/3, NS5/1 (combination 3)
Sequence 4a, 6e, 6b, 2e, 2g, NS4/3a, NS4/3b, NS5/1b (combination 4)
Sequence 4a, 6e, 6b, 2e, 2g, NS4/3, NS5/1, 9c (combination 5)
Sequence 4a, 2g, NS4/3, 2e, 6c, NS5/1, 9c (combination 6)
Sequence 4a, 6, 2e, 2g, 7A1, NS5/1 (combination 7)

The following sequences are described in P 42 09 215.9:

| Antigen | Sequence protocol in P 42 09 215.9 SEQ ID NO | Sequence protocol in the present application SEQ ID NO |
|---|---|---|
| 4a | 13 | 12 |
| 6b | 18 | 13 |
| 6e | 21 | 14 |
| 2e | 7 | 15 |
| 2g | 9 | 16 |
| 6c | 19 | 17 |
| 9c | 28 | 18 |
| 6 | 16 | 19 |

In these combinations, the antigens are preferably used in the following quantities:

| | Quantity in combination [ng/ml] | |
|---|---|---|
| Antigen | Segment | Preferred segment |
| 4a | 20–200 | 40–70 |
| 6e | 20–200 | 50–80 |
| 6b | 20–200 | 40–70 |
| 2e | 5–100 | 15–30 |
| 2g | 5–75 | 15–25 |
| NS4/3 | 10–120 | 25–40 |
| NS5/1 | 3–25 | 5–10 |
| 6c | 30–500 | 120–170 |
| NS4/3a | 20–200 | 45–60 |
| NS4/3b | 30–250 | 80–90 |
| NS5/1b | 40–400 | 120–140 |
| 9c | 100–1000 | 300–400 |
| 7A1 | 10–120 | 25–40 |
| 6 | 20–200 | 50–80 |
| 8C3 | 100–750 | 200–350 |

In a preferred manner, the antigens are used individually without being covalently bound to one another, or covalently bound with the aid of a peptide linker.

Owing to the increased sensitivity necessary for the infection parameter HCV, the preferred type of assay used for the detection is a heterogeneous immunoassay. These heterogeneous assays allow wash steps which significantly reduce the measuring signal background, thus increasing the sensitivity.

The determination can be carried out, for example, by means of a radioimmunoassay, enzyme-immunoassay or in an immunofluorescence procedure. In such a procedure, the peptide antigen is usually immobilized. The sample which is tested for anti-HCV antibodies is added and the antibodies bound to the antigen are determined via a labeled anti-human immunoglobulin antibody. The peptide antigen of the invention can be immobilized either adsorptively, directly or indirectly, via a carrier molecule (i.e. polymer, protein), covalently or via a biological binding pair such as biotin/streptavidin, antibody/antigen or sugar/lectin, where the peptide antigen is covalently bound to his partner.

In order to carry out the immunoassay, the peptide antigens of the invention can preferably be immobilized to beads, plastic vials or microtiter plates (preferably polystyrene or copolymers of polystyrene). The expert is familiar with these procedures. Immobilization is preferably achieved in that the peptide antigen is non-specifically adsorbed to the surface or covalently bound to functionalized or activated surfaces. The non-specific adsorption can be improved by linking the peptide antigen with the protein to form a conjugate which is then used for adsorption (see for example EP-A 0 269 092). Binding can also be achieved via an immobilized antibody. For this purpose, the peptide antigen should be modified such that the epitope is not blocked by the binding of the antibody, for example, by formation of a peptide protein conjugate.

Conjugation of the peptide antigen to the binding partner is preferably achieved via a spacer. Advantageously, this spacer contains 10–50, preferably 10–30 atoms, and it is preferably also an essentially linear molecule. Examples include spacers of alkyl, polyether or polyamide chains. In a particularly preferred embodiment, the peptide antigen of 4–9 amino acids in length is bound to a carrier via a linear spacer of 10–30 atoms in length. If a spacer is to be used which is made of amino acids, said spacer advantageously consists of amino acids which do not correspond to the sequence in direct vicinity of the peptide antigen in the HCV gene.

In a preferred embodiment, the peptide antigen of the invention is covalently bound to biotin and immobilization is achieved via an avidin/streptavidin solid phase, after, before or during the specific reaction with the serum antibodies to be detected.

Also suitable are methods where detection is not achieved via a labeled antibody, but via a labeled, additional peptide antigen which has one of the sequences contained in SEQ ID No. 1–20 or 22–28 or a partial sequence thereof.

The peptide antigens of the invention can be produced according to methods of synthesizing peptides which are known to the expert. Another subject matter of the invention is therefore a method of producing a peptide antigen of the invention wherein the amino acid which forms the C-terminal end is bound to a carrier, then the peptide antigen is gradually synthesized beginning at the C-terminal end and subsequently cleaved off from the carrier.

In detail, the carboxyl group of an amino acid is linked to an insoluble polymer which is easy to filtrate. The peptide chain is then gradually formed beginning at the C-terminal end. For this purpose, an N-protected amino acid is made to react with a reactive group of the synthetic resin. The N-protected group is removed from the amino acid which is covalently attached to the carrier particle, and the resulting amino acyl polymer is reacted with the next N-protected amino acid. The N-protected group is removed from the dipeptide which is also covalently attached to the carrier resin, and the resulting amino acyl polymer is reacted with the next N-protected amino acid. All excess reagents and by-products are removed in a simple filtration procedure. Once the desired peptide sequence is obtained in this manner, the covalent binding between the C-terminal amino acid and the anchor group of the polymer carrier is cleaved. In a simple filtration procedure the insoluble carrier is removed from the peptide which is now in solution. The peptide can be purified in any chromatographic procedure.

The peptide antigens of the invention can, for example, be produced according to Merrifield, JACS 85 (1964) 2146. Biotinylation, if necessary, can be accomplished according to PNAS USA 80 (1983) 4045. A preferred biotinylation agent is biotinyl amino caproic acid-N-hydroxysuccinimide ester, when the antigen is still protected and bound to the resin.

A preferred method for the preparation of a biotinylated peptide antigen is the incorporation of a biotin residue at the N-terminal end during a solid phase synthesis of the peptide antigen.

This method is preferably employed when the peptide antigen contains several ε-lysine amino groups which are not to be biotinylated. This is the case, for example, when N-α-Fmoc-N-ε-biotinyl-aminocaproyl lysine, N-α-Fmoc-N-ε-biotinyl lysine is used; or when the N-terminal amino acid is to be biotinylated, biotinyl amino caproic acid or dimethoxytrityl biotin is used with an activating reagent such as dicyclohexyl carbodiimide or as an activated ester.

In another preferred embodiment, a detection antibody which is directed against the Fc part of human IgG is immobilized. This is preferably achieved by using a monoclonal antibody. The peptide antigen is then in solution. The antibody to be detected (analyte) and all other antibodies of the sample liquid are bound by the wall antibody. The bound antibody can then bind the analyte which in turn can be detected with a suitable detection system, for example, in a competitive assay with the peptide antigen enzyme conjugate.

By employing immunization methods which are known to the expert, the peptide antigens of the invention can also be used to obtain antibodies to detect the virus itself in an immunological test.

Another subject matter of the invention is therefore a method of producing antibodies which is characterized in that a mammal is immunized with a peptide of the invention which, if necessary, is bound to a carrier. The antibodies are then obtained from the serum or the spleen according to known methods.

In a preferred embodiment, B-lymphocytes of these immunized animals are fused with a suitable cell line in the presence of transformed agents. The cell line which produces the desired antibodies is cloned, cultured, and the monoclonal antibodies are obtained from the cells or the culture supernatant.

With these antibodies it is possible to directly determine HCV viruses. Another subject matter of the invention is therefore a method of determining HCV viruses which is characterized in that the sample is incubated with an antibody of the invention under conditions allowing an antigen/antibody complex formation and the amount of formed antibody antigen complex is determined.

Another subject matter of the invention is a method of producing vaccines using the peptide antigens of the invention, and a vaccine for treating HCV infections, said vaccine containing as an immunogen at least one peptide antigen with the sequence shown in SEQ ID NO 1–11, 20, and 22–28, which can be carrier-bound, or a partial sequence thereof in a pharmacologically effective dose and in a pharmaceutically acceptable formulation.

These vaccines can be prepared according to known methods. In a preferred manner, however, the peptide antigens are first lyophilized and subsequently, if necessary, suspended under the addition of additives.

Vaccination with the vaccine of the invention or vaccine combinations can be done by the expert according to known methods such as intradermal, intramuscular, intraperitoneal, intravenous, subcutaneous and intranasal procedures.

For an intramuscular or subcutaneous administration, the vaccine can be suspended in a physiological saline solution, for example. In an intranasal or intraoccular application, the vaccine can be applied in the form of spray or an aqueous solution. In a local or oral administration, it is frequently necessary to temporarily protect the immunogens against inactivation, for example against proteolytic enzymes in the cavity of the mouth or the stomach. Such a temporary protection can, for example, be achieved by encapsulation of the immunogens. This encapsulation can be accomplished by coating with a protective agent (microencapsulation) or by embedding a multitude of immunogens of the invention in a protective carrier (macroencapsulation).

The encapsulation material used can be semipermeable or become semipermeable when introduced into the human or animal body. When such an encapsulation is applied, a biologically degradable substance is usually used as a carrier.

Also subject matter of the invention is an immunological method of determining infectious HCV sera by means of one or several peptide antigens, where there is used a peptide antigen from the carboxyl-terminal NS4 epitope of HCV, particularly outside of C100-3. The peptide with the SEQ ID NO 6 has proven to be particularly reactive. The term infectious sera refers to those sera where HCV RNA can be detected. This can be achieved, for example, in a polymerase chain reaction. These peptide antigens include in particular those that contain an amino acid sequence which is distinguished from SEQ ID No. 6 by not more than one amino acid, and which, as compared to SEQ ID No. 6, is shorter by no more than three amino acids or not longer by more than 25 amino acids or have the same length.

The following examples and sequence protocols explain the invention in greater detail.

The following references are used in the sequence protocols:

| Antigen | SEQ ID NO |
|---|---|
| 7B6 | 1 |
| 7A5 | 2 |
| NS5/1 | 3 |
| 7B12 | 4 |
| 6F10 | 5 |
| 7A1 | 6 |
| NSF/3a | 7 |
| NS4/3b | 8 |
| NS4/3 | 9 |
| 7D/2 | 10 |
| NS5/1b | 11 |
| 4a | 12 |
| 6b | 13 |
| 6e | 14 |
| 2e | 15 |
| 2g | 16 |
| 6c | 17 |
| 9c | 18 |
| 6 | 19 |
| 8C3 | 20 |
| B3 | 21 |
| B4 | 22 |
| B5 | 23 |

| Antigen | SEQ ID NO |
|---------|-----------|
| B6 | 24 |
| D1 | 25 |
| D2 | 26 |
| D3 | 27 |
| X | 28 |

EXAMPLE 1

Synthesis of H-SRRFAQALPVWARPD-OH(NS5/1)

The peptide was produced by means of Fmoc (fluorenylmethoxycarbonyl) solid phase synthesis. The reactions were carded out in a Labortec (Switzerland) SP 640 peptide synthesizer. With respect to the Fmoc amino acid derivative, the coupling reactions were carded out with 2.4 equivalents of dicyclohexylcarbodiimide and 2.2 equivalents of N-hydroxybenzotriazol over 90 minutes. The reaction medium used was dimethylformamide. The Fmoc group was cleaved with 20% Piperiden in DMF in 10 and 20 minutes. 2.0 equivalents of the following amino acid derivatives were used: Pro, Arg(with PMC (pentamethylchromane) protective group), Ser(with tert. butyl protective group), Trp, Asp(with tert. butyl ester protective group), Phe, Ala, Gln, Leu, Val. The coupling reactions were repeated with half of the reagents. The successful coupling was checked with the Kaiser-test (Anal. Biochemistry 34 (1970) 595), and the resin coating was determined via UV absorption of the released fulven groups after each piperidine cleavage. The peptide was synthesized to 5 g of Wang resin (polystyrene/1% divinylbenzene) with a charge of 0.50 mmol/g (JAGS 95 (1973) 1328). After the synthesis, the degree of charge was only at 0.39 mmol/g.

The peptide was released with 200 ml trifluoro acetic acid, 200 ml dichloromethane, 10 ml ethane dithiol, 10 ml m-cresol, 5 ml ethyl methyl sulfide and 5 ml water in 30 minutes at room temperature. The cleaving solution was concentrated several times with toluene, then the peptide was precipitated with diethyl ether.

To remove the scavengers and other smaller molecules, the raw material was purified in a Sephadex G10 column. 2.4 g of material with a of 31% purity (RP-HPLC) were obtained after lyophilization. To bring the material to a final purity of >95%, 250 mg peptide were purified over a preparative RP-HPLC column (40 mm×250 mm) which was filled with C18 material (5 micrometer, 300 Ångstrom) and a water/trifluoro acetic acid, acetonitrile/trifluoro acetic acid gradient. 48 mg of a 95.2% (HPLC) white material were obtained after lyophilization. The identity of the material was checked via FAB-MS.

EXAMPLE 2

For the biotinylation of the peptide antigen from example 1, one highly concentrated mol equivalent (solubility depends on the amino acid sequence) was dissolved in argon-saturated potassium phosphate buffer (0.1 mol/l, pH 8.0), and 3 equivalents of D-biotinyl-ε-aminocaproic acid-N-hydroxysuccinimide ester dissolved in argon-saturated dimethylformamide (solution of 1 μmol reagent in 5 μl DMF) were added.

The reaction mixture was stirred for 2 hours at room temperature under argon under permanent control via analytic RP-HPLC. Once <5% educt were present, the reaction mixture was directly applied onto a preparative RP-HPLC column, and the product material was purified via a 0.1% trifluoro acetic acid/water to 0.1% trifluoro acetic acid/acetonitrile gradients (slope: 0% to 100% in 90 minutes). The product material was obtained by concentration and lyophilization of the product fractions. The yields ranged between 40% and 90%. In the analysis procedure, purity was checked via HPLC, HPCE and TLC; identity was checked with LSI-MS (molpeak) and TLC with specific dye reagents (p-dimethyl amino cinnamic aldehyde on biotin) and the contents were determined in by microanalysis (Nitrogen).

EXAMPLE 3

HCV antibodies were determined in a two-step sandwich immunoassay for the detection reaction. Reagents of the following composition:

Reagent 1:

Combinations 1–6 of peptide antigens, biotinylated peptide antigens or non-biotinylated peptide antigens.

40 mmol/l phosphate buffer pH 7.0

0.9 weight % NaCl 10 vol. % bovine serum

Reagent 2:

20 mU/ml of a conjugate of polyclonal antibodies to human immunoglobulin (sheep) and peroxidase 40 mmol/l phosphate buffer pH 7.0

0.05 weight-% Tween® 20

0.2% bovine serum albumin 0.2% bovine IgG 1 ml reagent 1 and 10 μl or 20 μl sample were incubated for 1 h at room temperature in a streptavidin-coated polystyrene vial (manufactured according to example 1 of EP-A 0 344 578). Subsequently, the mixture was washed 3 times with tap water and incubated with 1 ml reagent 2 for 1 h at room temperature. Subsequently, the mixture was washed 3 times with tap water. 1 ml ABTS® (2,2'-azino-di-[3-ethylbenzthiazolin sulfonate(6)]-diammonium salt, 1.9 mmol/l, in 100 mmol/l phosphate citrate buffer pH 4.4 with 3.2 mmol/l sodium perborate) were added for the detection reaction. After 60 minutes the absorbance can be photometrically measured at 420 nm. The results are given in Tables I, II, and III.

Explanation of the symbols used in the tables:

−/+: negative/positive (the cut-off for a positive signal in an ELISA is defined as the mean absorbance at 420 nm plus 3 standard deviations of a collective of 10 negative control sera. The samples were measured at a sample dilution of 1:250).

The following antigen concentrations were used:

a) As an individual antigen in the test

| Antigen | Quantity [ng/ml] |
|---------|------------------|
| 7B6 | 200 |
| 7A5 | 200 |
| NS5/16 | 130 |
| NS5/1 | 85 |
| 7D2 | 200 |
| 7B12 | 200 |
| 6F10 | 70 |
| 7A1 | 200 |
| 8C3 | 300 | b) in the combination

| Antigen | \multicolumn{7}{c}{Amount [ng/ml] in combination} |
| | 1 | 2 | 3 | 4 | 5 | 6 | 7 |
| --- | --- | --- | --- | --- | --- | --- | --- |
| 4a | 52 | 65 | 52 | 50 | 50 | 52 | 52 |
| 6e | 58 | 73 | — | 58 | 55 | — | — |
| 6b | 52 | 65 | — | 50 | 50 | — | — |
| 2e | 20 | 25 | 20 | 20 | 18 | 20 | 20 |
| 2g | 17 | 21 | 17 | 17 | 15 | 17 | 17 |
| NS4/3 | 30 | 38 | 30 | — | 27 | 30 | — |
| NS5/1 | 7 | — | 7 | — | 7 | 7 | 7 |
| 6c | — | — | 150 | — | — | 150 | — |
| NS4/3a | — | — | — | 51 | — | — | — |
| NS4/3b | — | — | — | 83 | — | — | — |
| NS5/1b | — | — | — | 130 | — | — | — |
| 9c | — | — | — | — | 350 | 350 | — |
| 7A1 | — | — | — | — | — | — | 30 |
| 6 | — | — | — | — | — | — | 65 |

TABLE I

| Serum | NS4/3a | NS4/3b | NS4/3 | 7A1 | 7B6 | 7A5 | NS5/1b | NS5/1 | 7D2 | 7B12 | 6F10 |
| --- | --- | --- | --- | --- | --- | --- | --- | --- | --- | --- | --- |
| 1 | + | + | + | + | — | — | — | — | — | — | — |
| 2 | + | — | — | — | — | — | + | + | — | — | — |
| 3 | + | + | + | + | — | — | — | — | — | — | + |
| 4 | — | — | — | — | — | — | — | — | — | — | — |
| 5 | + | + | + | + | — | — | — | — | — | — | — |
| 6 | — | + | + | + | — | — | + | + | — | — | + |
| 7 | — | — | — | — | — | — | — | — | — | — | — |
| 8 | + | + | + | + | — | — | — | — | — | — | — |
| 9 | + | + | + | + | — | — | — | + | — | — | + |
| 10 | + | — | + | + | — | — | — | — | — | — | — |
| 11 | + | + | + | + | — | — | + | + | — | — | — |
| 12 | + | + | + | + | — | — | — | — | — | — | — |
| 13 | — | — | + | + | — | — | + | + | + | + | — |
| 14 | — | — | — | — | — | — | — | — | — | — | — |
| 15 | + | + | + | + | — | — | — | — | — | — | — |
| 16 | + | + | + | + | — | — | — | — | + | — | + |
| 17 | + | + | + | + | — | + | — | — | — | — | — |
| 18 | + | + | + | + | — | — | — | — | — | — | — |
| 19 | — | — | — | — | — | — | — | — | — | — | — |
| 20 | — | — | + | + | — | — | — | — | — | — | — |
| 21 | + | + | + | + | — | — | — | — | — | — | — |
| 22 | — | + | + | + | — | — | — | — | — | — | — |
| 23 | + | + | + | + | — | — | + | + | — | + | — |
| 24 | + | + | + | + | — | — | + | + | — | — | — |
| 25 | + | + | + | + | + | + | + | + | — | — | + |

TABLE II

| Serum | \multicolumn{6}{c}{Antigen mixture} |
| | 1 | 2 | 3 | 4 | 5 | 6/7 |
| --- | --- | --- | --- | --- | --- | --- |
| 1 | + | + | + | + | + | + |
| 2 | + | + | + | + | + | + |
| 3 | + | + | + | + | + | + |
| 4 | + | + | + | + | + | + |
| 5 | + | + | + | + | + | + |
| 6 | + | + | + | + | + | + |
| 7 | + | + | + | + | + | + |
| 8 | + | + | + | + | + | + |
| 9 | + | + | + | + | + | + |
| 10 | + | + | + | + | + | + |
| 11 | + | + | + | + | + | + |
| 12 | + | + | + | + | + | + |
| 13 | — | — | — | — | — | — |
| 14 | — | — | — | — | — | — |
| 15 | + | + | + | + | + | + |
| 16 | — | — | +/− | — | — | +/− |
| 17 | + | + | + | + | + | + |
| 18 | + | + | + | + | + | + |
| 19 | — | — | +/− | — | — | +/− |
| 20 | + | + | + | + | + | + |
| 21 | — | — | +/− | — | — | +/− |
| 22 | — | — | — | — | — | — |
| 23 | + | + | + | + | + | + |
| 24 | + | + | + | + | + | + |
| 25 | + | + | + | + | + | + |

TABLE III

| Serum | Antigens 8C3 |
| --- | --- |
| B1 | — |
| B2 | — |
| B3 | + |
| B4 | +/− |
| B5 | — |
| B6 | — |
| B7 | +/− |
| B8 | + |
| B9 | + |
| B10 | + |
| B11 | — |
| B12 | — |
| B13 | + |
| B14 | + |
| B15 | — |
| B16 | — |
| B17 | + |
| B18 | + |
| B19 | + |

TABLE III-continued

| Serum | Antigens 8C3 |
|---|---|
| B20 | + |
| S25 | + |
| 01 | − |
| 56 | + |
| Negative-control | − |

EXAMPLE 4

In a study with clinical samples, 9 infectious sera were found by employing PCR and further analyzed in an immunoassay. Two of the samples were detected with a conventional antigen mixture (c22-3, c33c, c100-3). With peptide 7A1, it was possible to detect an additional serum.

| Sample No. | PCR | HCV-Antigens (c22-3, c33c, c100-3) | 7A1 |
|---|---|---|---|
| 1 | +/+ | − | − |
| 2 | +/+ | − | + |
| 3 | +/+ | +++ | +++ |
| 4 | +/+ | − | − |
| 5 | +/+ | ++ | +++ |
| 6 | +/+ | − | − |
| 7 | +/+ | − | − |
| 8 | +/+ | − | − |
| 9 | +/+ | − | − |

EXAMPLE 5

With peptide 7A1 it was possible to detect 5 infectious sera out of 2000 donor specimen. Only two thereof were identified with a conventional antigen mixture (c22-3, c33c, c100-3).

TABLE IV

| Sample No. | PCR | HCV-Antigens (c22-3, c33c, c100-3) | 7A1 |
|---|---|---|---|
| 1 | +/+ | +++ | ++ |
| 2 | +/+ | +++ | + |
| 3 | +/− | − | + |
| 4 | +/− | − | +/− |
| 5 | +/− | − | ++ |

EXAMPLE 6

Epitope in the core region

The following is a description of a new dominant HCV antigen in the core region. This antigen could not be found with classic methods, but only with the aid of biotinylated peptides corresponding to example 2 and by testing the ability of the individual biotinylated peptides to form immunocomplexes with the antibodies of sera that were shown to be HCV-positive. These peptides are particularly useful in methods where soluble peptide antigens are used. They are, however, less useful in those methods where peptide antigens are directly bound to a solid phase.

The longest sequence is antigen X (SEQ. I.D. No. 28). The shortest and most reactive sequence is D2 (SEQ ID NO 26). The most reactive antigen (greatest signal in the immunoassay according to example 3) is D1 (SEQ ID NO 25). A residual reactivity is also found in D3 (SEQ ID NO 27). The sequences were tested with 26 HCV-positive sera and all showed a distinct reaction (24 sera>500 mA, one>300 mA, and one>150 mA). However, they did not show a reaction with negative serum (70 mA). The antigens B3 (SEQ ID No. 21), B4 (SEQ ID NO 22), B5 (SEQ ID NO 23), and B6 (SEQ ID NO 24) were also tested, and the dependency of the signal height upon the antigen concentration was measured. The resulting typical concentration for use of the antigens B4 to B6 ranges between 150–200 μm/ml in tests corresponding to example 3. B3 is not reactive.

The results of the tests of the above-mentioned new peptides are given in Tables VI and VII. For each test, 50 ng of the antigen were used in 100 μl incubation buffer. The sera were diluted 1:60. The reactivities mean:

TABLE VI

| Serum | Antigens | | | |
|---|---|---|---|---|
| | B4 | B5 | B6 | reference peptide |
| neg | — | — | — | — |
| 071 | +++ | ++ | +++ | + |
| 075 | n.b. | n.b. | n.b. | n.b. |
| 575 | +++ | +++ | +++ | — |
| 004 | +++ | +++ | +++ | — |
| 069 | +++ | +++ | ++ | — |
| 56- | +++ | +++ | +++ | — |
| B1 | +++ | ++ | ++ | — |
| B2 | +++ | ++ | +++ | — |
| B3 | +++ | ++ | ++ | ++ |
| B4 | +++ | ++ | ++ | — |
| B5 | +++ | +++ | ++ | — |
| B6 | ++ | ++ | ++ | — |
| B7 | ++ | ++ | ++ | — |
| B8 | ++ | +++ | +++ | — |
| B9 | ++ | +++ | ++ | — |
| B10 | +++ | +++ | +++ | + |
| B11 | ++ | ++ | ++ | — |
| B12 | n.b. | n.b. | n.b. | n.b. |
| B13 | ++ | +++ | +++ | — |
| B14 | ++ | +++ | +++ | — |
| B15 | ++ | ++ | ++ | — |
| B16 | ++ | ++ | ++ | + |
| B17 | ++ | +++ | +++ | — |
| B18 | ++ | +++ | +++ | — |
| B19 | ++ | +++ | +++ | ++ |
| B20 | ++ | + | + | — |

+: 70–140 mA
++: 40–500 mA
+++: >500 mA

TABLE VII

| Serum | Antigens | | | |
|---|---|---|---|---|
| | D1 GVYLLPRR | D2 VYLLPR | D3 YLLP | reference peptide |
| neg | — | — | — | — |
| 071 | +++ | ++ | + | — |
| 075 | +++ | ++ | ++ | — |
| 575 | +++ | ++ | + | — |
| 004 | +++ | ++ | ++ | — |
| 069 | +++ | + | — | — |
| 56- | +++ | ++ | — | — |
| B1 | +++ | ++ | ++ | — |
| B2 | +++ | ++ | ++ | — |
| B3 | +++ | ++ | ++ | — |
| B4 | +++ | ++ | + | — |
| B5 | +++ | ++ | ++ | — |
| B6 | +++ | ++ | — | — |
| B7 | +++ | ++ | ++ | — |
| B8 | +++ | ++ | +/− | — |
| B9 | +++ | +++ | +++ | — |

TABLE VII-continued

| | Antigens | | | |
|---|---|---|---|---|
| Serum | D1 GVYLLPRR | D2 VYLLPR | D3 YLLP | reference peptide |
| B10 | +++ | +++ | +++ | + |
| B11 | +++ | ++ | + | + |
| B12 | + | + | — | — |
| B13 | +++ | +++ | — | — |
| B14 | +++ | +++ | +++ | — |
| B15 | ++ | ++ | — | — |
| B16 | +++ | ++ | — | — |
| B17 | +++ | +++ | ++ | — |
| B18 | +++ | ++ | +/− | — |
| B19 | +++ | +++ | + | — |
| B20 | ++ | ++ | + | — |

---

We claim:

1. Isolated peptide selected from the group consisting of:
   (i) SEQ ID NO: 1;
   (ii) SEQ ID NO: 2;
   (iii) SEQ ID NO: 3;
   (iv) SEQ ID NO: 4;
   (v) SEQ ID NO: 5;
   (vi) SEQ ID NO: 6; and
   (vii) SEQ ID NO: 20.

2. Isolated peptide selected from the group consisting of: SEQ ID NO: 27 and SEQ ID NO: 9.

3. Composition of matter comprising a plurality of peptides, said composition being selected from the group consisting of:
   (a) a mixture of SEQ ID NOS: 3, 9, 12, 13, 14, 15 and 16;
   (b) a mixture of SEQ ID NOS: 9, 12, 13, 14, 15 and 16;
   (c) a mixture of SEQ ID NOS: 3, 9, 12, 15, 16 and 17;
   (d) a mixture of SEQ ID NOS: 7, 8, 11, 12, 13, 14, 15 and 16;
   (e) a mixture of SEQ ID NOS: 3, 9, 12, 13, 14, 15, 16 and 18;
   (f) a mixture of SEQ ID NOS: 3, 9, 12, 15, 16, 17 and 18; and
   (g) a mixture of SEQ ID NOS: 3, 6, 12, 15, 16 and 19.

4. A complex comprising the isolated peptide of claim 1, covalently coupled to a protein or to a peptide which is a non-hepatitis C virus protein or peptide.

5. The complex of claim 4, wherein said non-hepatitis C virus protein or peptide is biotinylated.

* * * * *

UNITED STATES PATENT AND TRADEMARK OFFICE
CERTIFICATE OF CORRECTION

PATENT NO. : 5,674,676
DATED : October 7, 1997
INVENTOR(S) : Seidel et al.

It is certified that error appears in the above-indentified patent and that said Letters Patent is hereby corrected as shown below:

In column 1, line 54, change "qualifies" to -- qualities --.

In column 7, line 16, change "carded" to -- carried --.

In column 7, line 18, change "carded" to -- carried --.

In column 7, line 34, change "JAGS" to -- JACS --.

In column 11, Table IV, in the second line beneath the caption "7A1", change "+" to -- +++ --.

In column 12, lines 17-19, insert -- + : 70-140 mA
++ : 40-500mA
+++ : > 500 mA --.

In column12, lines 45-47, delete " + : 70-140 mA
++ : 40-500mA
+++ : > 500 mA ".

Signed and Sealed this

Twenty-third Day of November, 1999

Attest:

Q. TODD DICKINSON

*Attesting Officer*  *Acting Commissioner of Patents and Trademarks*

UNITED STATES PATENT AND TRADEMARK OFFICE
CERTIFICATE OF CORRECTION

PATENT NO. : 5,674,676
DATED : October 7, 1997
INVENTOR(S) : SEIDEL et al.

It is certified that error appears in the above-identified patent and that said Letters Patent is hereby corrected as shown below:

In column 6, in the table, in the seventh line beneath the caption "antigen", change "NSF/3a" to -- NS4/3a --.

In column 10, Table II (cont.), in the first line beneath the caption "1", change " - " to -- + --.

Signed and Sealed this

Fifteenth Day of February, 2000

Q. TODD DICKINSON

Attest:

Attesting Officer

Commissioner of Patents and Trademarks